United States Patent [19]

Heidenreich et al.

[11] Patent Number: 4,921,872
[45] Date of Patent: May 1, 1990

[54] ACARICIDAL AGENTS BASED ON AZOMETHINES OF 2,3-DIAMINOMALEIC ACID NITRILE

[75] Inventors: Holger Heidenreich, Kuden; Benedikt Becker, Mettmann, both of Fed. Rep. of Germany

[73] Assignee: Bayer Aktiengesellschaft, Leverkusen, Fed. Rep. of Germany

[21] Appl. No.: 149,244

[22] Filed: Jan. 27, 1988

[30] Foreign Application Priority Data

Feb. 11, 1987 [DE] Fed. Rep. of Germany ....... 3704154
Aug. 6, 1987 [DE] Fed. Rep. of Germany ....... 3726044

[51] Int. Cl.$^5$ ............... C07C 121/45; A01N 37/34; A01N 41/10
[52] U.S. Cl. .................. 514/523; 514/641; 558/391
[58] Field of Search ................ 558/391; 514/641, 523

[56] References Cited

U.S. PATENT DOCUMENTS 3,912,724 10/1975 Begland ........................... 558/391
3,914,276 10/1975 Begland ........................... 558/391
4,002,616 1/1977 Neumer ........................... 558/391

FOREIGN PATENT DOCUMENTS 2438400 2/1975 Fed. Rep. of Germany .

OTHER PUBLICATIONS

The Journal of Organic Chemistry, vol. 39, 1974, May–Aug., pp. 2341 to 2350.
Patent Abstracts of Japan—3-28-77—C–Section (of Kokai #51-151325).

Primary Examiner—Joseph Paul Brust
Assistant Examiner—M. S. Howard
Attorney, Agent, or Firm—Sprung Horn Kramer & Woods

[57] ABSTRACT

A method of combating acarids which comprises applying to such acarids or to an acarid habitat an acaricidally effective amount of an azomethine of 2,3-diaminomaleic acid nitrile of the formula

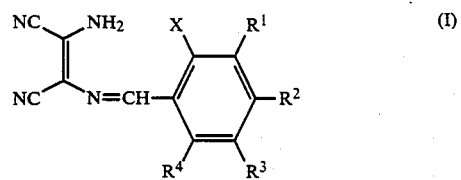

(I)

in which X represents halogen, halogenoalkyl or CN and $R^1$, $R^2$, $R^3$ and $R^4$ can be identical or different and represent hydrogen, optionally substituted alkyl, optionally substituted alkoxy, halogen, CN, $NO_2$, optionally substituted dialkylamino, alkoxycarbonyl, optionally substituted alkylthio, optionally substituted alkylthionyl, optionally substituted alkylsulphonyl, OH, SH or $NH_2$. The compounds other than the 2-chloro-and 2,6-dichloro-toluylideneamino-compounds are new.

12 Claims, No Drawings

ACARICIDAL AGENTS BASED ON AZOMETHINES OF 2,3-DIAMINOMALEIC ACID NITRILE

The present invention relates to the use of azomethines (=Schiff's bases), some of which are known, of 2,3-diaminomaleic acid nitrile as agents for combating pests, in particular as acaricides.

The invention furthermore relates to new azomethines (=Schiff's bases) of 2,3-diaminomaleic acid nitrile and a process for their preparation.

It is already known that azomethines of 2,3-diaminomaleic acid nitrile have bactericidal, viricidal and germicidal activities, such as, for example, aminotoluylideneamino-maleic acid nitrile (in this context, see, for example, Japanese Patent 51,151,325).

Azomethines of 2,3-diaminomaleic acid nitrile which contain certain chlorine-substituted phenyl groups (amino-2-chlorotoluylideneamino-maleic acid nitrile and amino-2,6-dichlorotoluylideneaminomaleic acid nitrile) are furthermore known from the publication by R. W. Bagland et al. J. Org. Chem. 39, No. 16 (1974), page 2341 et seq.

However, nothing has as yet been disclosed about an activity of the abovementioned class of compounds against animal pests, in particular against spider mites.

It has now been found that the azomethines, some of which are known, of 2,3-diamino-maleic acid nitrile of the formula

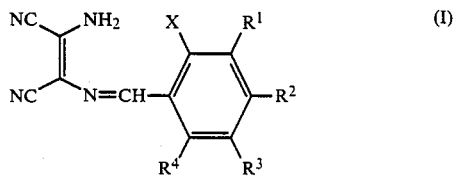

in which

X represents halogen, halogenoalkyl or CN and
$R^1$, $R^2$, $R^3$ and $R^4$ can be identical or different and represent hydrogen, optionally substituted alkyl, optionally substituted alkoxy, halogen, CN, $NO_2$, optionally substituted dialkylamino, alkoxycarbonyl, optionally substituted alkylthio, optionally substituted alkylthionyl, optionally substituted alkylsulphonyl, OH, SH or $NH_2$, have very pronounced acaricidal properties.

The azomethines, some of which are known, of 2,3-diaminomaleic acid nitrile of the formula (I)

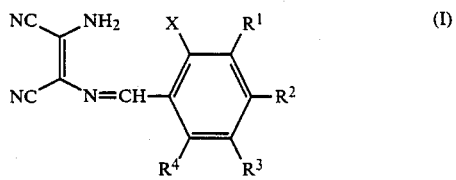

in which

X represent halogen, halogenoalkyl or CN and $R^1$, $R^2$, $R^3$ and $R^4$ can be identical or different and represent hydrogen, optionally substituted alkyl, optionally substituted alkoxy, halogen, CN, $NO_2$, optionally substituted dialkylamino, alkoxycarbonyl, optionally substituted alkylthio, optionally substituted alkylthionyl, optionally substituted alkylsulphonyl, OH, SH or $NH_2$, are obtained by a process in which 2,3-diamino-maleic acid nitrile ("DAMN") of the formula

is reacted with an aldehyde of the formula

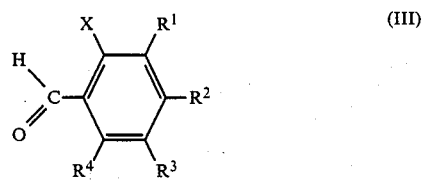

in which

X, $R^1$, $R^2$, $R^3$ and $R^4$ have the abovementioned meaning, in molar amounts in a suitable diluent.

Surprisingly, the azomethines, some of which are known, of the formula (I) have an acaricidal activity. Such an activity has not previously been disclosed for the substance class of azomethines of diaminomaleic acid nitrile. The use of the compounds of the formula (I) as acaricides thus represents an enrichment of the prior art.

The compounds of the general formula (I) can exist in the stereoisomeric cis- and/or trans-forms, for example

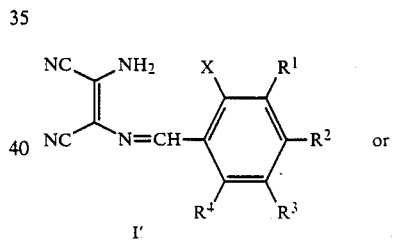

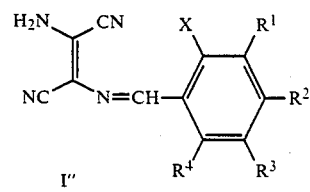

However, the compounds are preferably in the cis-form (I').

Formula (I) provides a general definition of the azomethines.

In formula (I), X preferably represents fluorine, chlorine, bromine, iodine, $CF_3$ or CN.

In the radicals $R^1$, $R^2$, $R^3$ and $R^4$, preferred possible substituents for alkyl, alkoxy, dialkylamino, alkylthio, alkylthionyl and alkylsulphonyl are: halogen, in particular fluorine, chlorine and bromine, and OH and $NH_2$.

Compounds of the formula (I) which are preferably used are those in which

X and $R^4$ can be identical or different and represent fluorine, chlorine, bromine, iodine, $CF_3$ or CN and
$R^1$, $R^2$ and $R^3$ can be identical or different and represent hydrogen, alkyl($C_1$-$C_4$), halogenoalkyl(-

$C_1$–$C_4$), alkoxy ($C_1$–$C_4$), halogenoalkoxy($C_1$–$C_4$), halogen, CN, $NO_2$, dialkyl($C_1$–$C_4$)amino, alkoxy($C_1$–$C_4$)carbonyl, alkyl($C_1$–$C_4$)thio, alkyl($C_1$–$C_4$)thionyl, dihalogenoalkyl($C_1$–$C_4$)amino, alkyl($C_1$–$C_4$)sulphonyl, OH, SH or $NH_2$.

Compounds which are particularly preferably used are those of the general formula Ia

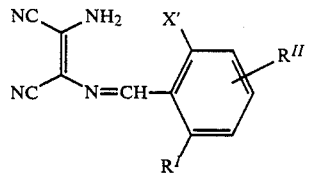

(Ia)

in which
  x' and $R^I$ can be identical or different and represent fluorine, chlorine, bromine, iodine or $CF_3$ and
  $R^{II}$ represents hydrogen, chlorine, bromine, iodine, cyano, nitro, methyl, ethyl, n- or i-propyl, n-, i-, s- or t-butyl, methoxy, ethoxy, methoxycarbonyl, ethoxycarbonyl, trifluoromethyl, trichloromethyl, pentafluoroethyl, trifluoroethyl, trifluoromethyl sulphone, trifluoromethoxy, trichloromethoxy, pentafluoroethoxy, dimethylamino, diethylamino, di-β-chloroethylamino or di-β-hydroxyethylamino.

Compounds which are especially preferably used are those of the formula Ib

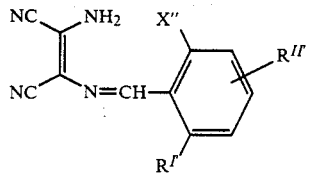

(Ib)

in which
  X" and $R^{I'}$ can be identical or different and represent chlorine or bromine and
  $R^{II'}$ represents chlorine, bromine, iodine, hydrogen, cyano, nitro, methyl, ethyl, n- or i-propyl, methoxy, ethoxy, methoxycarbonyl, ethoxycarbonyl, trifluoromethyl, trichloromethyl, dimethylamino, diethylamino or trifluoromethyl sulphone.

Compounds which are especially preferably used are those of the formula Ic

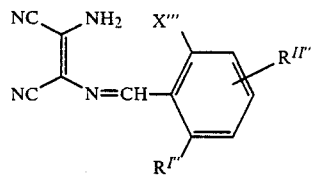

(Ic)

in which
  X''' and $R^{I''}$ can be identical or different and represent chlorine or bromine and
  $R^{II''}$ represents hydrogen, chlorine, bromine, methyl, cyano, trichloromethyl, trifluoromethyl, methoxy, trifluoromethoxy, trichloromethoxy or trifluoromethyl sulphone.

Compounds which are exceptionally preferably used are those of the general formula Id

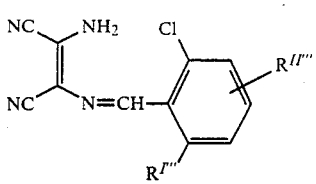

(Id)

in which
  $R^{I'''}$ represents chlorine or bromine and
  $R^{II'''}$ represents hydrogen, chlorine, methyl, trichloromethyl, methoxy, trichloromethoxy or trifluoromethoxy.

The compound of the formula

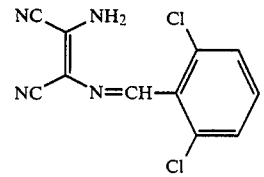

is mentioned exceptionally preferably used.

The following azomethines of the general formula (I) may be mentioned specifically, in addition to the compounds mentioned in the preparation examples:

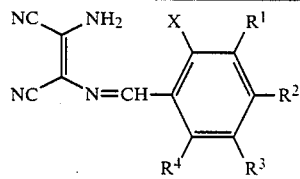

(I)

| X | $R^1$ | $R^2$ | $R^3$ | $R^4$ |
|---|---|---|---|---|
| Br | H | H | H | Br |
| Cl | $CH_3$ | H | H | Cl |
| Cl | $C_2H_5$ | H | H | $CH_3$ |
| Cl | $CH_3$ | H | H | $CH_3$ |
| Br | H | Br | H | H |
| Br | H | H | Br | H |
| Cl | H | H | H | Br |
| Cl | H | $C_2H_5$ | H | $CH_3$ |
| Cl | H | H | H | $C_2H_5$ |
| $CF_3$ | H | H | H | Cl |
| $CF_3$ | H | H | H | $CF_3$ |
| Cl | H | F | H | Cl |

The present invention also relates to new azomethines of 2,3-diaminomaleic acid nitrile of the formula

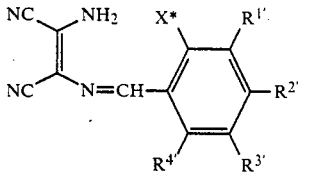

(I')

in which
  X* represents halogen, halogenoalkyl or CN and
  $R^{1'}$, $R^{2'}$, $R^{3'}$ and $R^{4'}$ can be identical or different and represent hydrogen, optionally substituted alkyl, optionally substituted alkoxy, halogen, CN, $NO_2$, optionally substituted dialkylamino, alkoxycarbonyl, optionally substituted alkylthio, optionally substituted alkylthionyl, optionally substituted alkylsulphonyl, OH, SH or NH$_2$,
wherein the radical

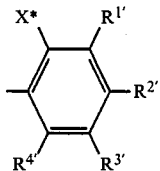

must not represent 2-chlorophenyl and must not represent 2,6-dichlorophenyl. The new compounds of the formula

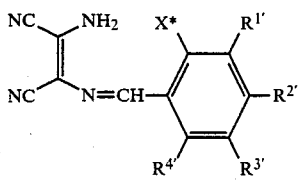

(I')

in which X*, R$^{1'}$, R$^{2'}$, R$^{3'}$ and R$^{4'}$ have the abovementioned meaning, are obtained by a process in which 2,3-diaminomaleic acid nitrile ("DAMN") of the formula

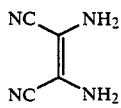

(II')

is reacted with an aldehyde of the formula

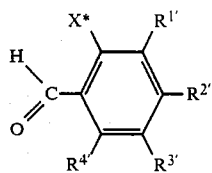

(III')

in which X*, R$^{1'}$, R$^{2'}$, R$^{3'}$ and R$^{4'}$ have the abovementioned meaning, in molar amounts in a suitable diluent.

Preferred compounds of the formula (I') are those in which

X* represents chlorine, fluorine, bromine, iodine, CF$_3$ or CN,

R$^{4'}$ represents hydrogen, chlorine, fluorine, bromine, iodine, CF$_3$ or CN and R$^{1'}$, R$^{2'}$ and R$^{3'}$ can be identical or different and represent hydrogen, alkyl (C$_1$-C$_4$), halogenoalkyl (C$_1$-C$_4$), alkoxy (C$_1$-C$_4$), halogenoalkoxy (C$_1$-C$_4$), halogen, CN, NO$_2$, dialkyl(C$_1$-C$_4$)amino, alkoxy(C$_1$-C$_4$)-carbonyl, alkyl(C$_1$-C$_4$)thio, alkyl(C$_1$-C$_4$)thionyl, dihalogenoalkyl(C$_1$C$_4$)amino, alkyl(C$_1$-C$_4$)sulphonyl, OH, SH or NH$_2$, wherein the radical

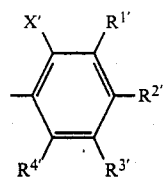

must not represent 2,6-dichlorophenyl or 2-chlorophenyl.

If, for example, 2,3-diaminomaleic acid nitrile (DAMN) and 2,4-dichlorobenzaldehyde are used as starting substances, the preparation process according to the invention can be represented as follows:

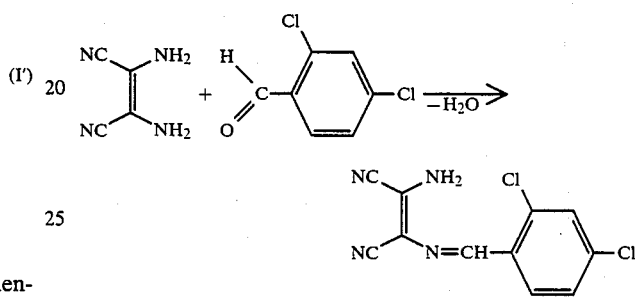

The formulae (III) and (III') provide general definitions of the aldehydes required as starting substances for carrying out the process for the preparation of the compounds (I) and (I'). These aldehydes are essentially known compounds. In this case, see, for example, O. Bayer, in Houben-Weyl, Volume VII/1, pages 16–36 (1954).

The other starting compound 2,3-diaminomaleic acid nitrile (II) is also known from the literature and is commercially available.

Possible diluents for carrying out the process for the preparation of compounds (I) or (I') are preferably polar organic solvents, such as, for example, alcohols (in particular methanol, ethanol or propanol (n and i)), dimethylformamide (DMF), dimethylsulphoxide (DMSO), hexemethylphosphoric acid triamide (HMPT) and acetonitrile.

The reaction temperature is in general in the range between about 0° C. and not more than the boiling point of the particular solvent, and the reaction is carried out in particular at temperatures from about 20° to about 100° C.

The reaction is preferably carried out under normal pressure.

For carrying out the process for the preparation of the compounds (I) and (I'), equimolar amounts of the reaction partners (II) and (III) or (III') are preferably reacted with one another. However, it is also possible for a slight excess of one of the two reactants to be used.

In a preferred embodiment, the two reaction partners are brought together in the diluent at room temperature and the mixture is then heated under reflux.

Working up is carried out by customary methods, the reaction product preferably being filtered off with suction, after cooling, and worked up by methods which are known per se.

The active compounds are suitable for combating animal pests, in particular mites (Acarina), encountered in agriculture, in forestry, in the preservation of stored products and materials and in the hygiene sector, and have a good plant tolerance and favorable toxicity to warm-blooded animals. They are active against normally sensitive and resistant species and against all or some stages of development. The abovementioned pests include:

From the order of the Acarina, for example, Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp, Sarcoptes spp., Tarsonemus spp., Bryobia praetiosa, Panonychus spp. and Tetranychus spp..

The active compounds (I) and (I') have an action not only against plant pests, hygiene pests and pests of stored products, but also in the veterinary medicine sector against animal parasites (ectoparasites), such as scaly ticks, leather ticks, scab mites and running mites.

They are active against normally sensitive and resistant species and strains and against all parasitisizing and non-parasitisizing stages of development of the ectoparasites.

The active compounds (I) and (I') are distinguished by a high acaricidal activity. they can be used particularly successfully against mites which damage plants, such as, for example, against the common spider mite (Tetranychus urticae).

The compounds of the formulae (I) and (I') moreover also have a fungicidal activity.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lingninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds (1) and (1') can be present in their commercially available formulations and in the use forms, prepared from these formulations, as a mixture with other active compounds, such as insecticides, baits, sterilizing agents, acaricides, nematicides or fungicides. The insecticides include, for example, phosphates, carbamates, carboxylates, chlorinated hydrocarbons, phenylureas, substances produced by microorganisms inter alia.

The active compounds (1) and (1') can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The active compounds which can be used according to the invention are also suitable for combating mites, ticks and the like in the field of animal husbandry and livestock breeding, it being possible to achieve better results, for example higher milk yields, a heavier weight, a more attractive animal coat, a longer life and the like, by combating the pests.

The active compounds which can be used according to the invention are employed in this field in a known manner, for example by oral use in the form of, for example, tablets, capsules, drinks or granules, by dermal or external use in the form if, for example, dips, sprays, pour-on and spot-on formulations and dusting, and by parenteral use in the form of, for example, the injections, and furthermore by the "feed-through" process.

Use as shaped articles (neck collar, ear tag) is moreover also possible.

PREPARATION EXAMPLES

Example 1 (new compound)

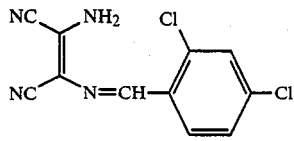

10.8 g of 2,3-diamino-maleic acid nitrile are heated under reflux with 17.5 g of 2,4-dichlorobenzaldehyde in 100 ml of ethanol. After 3 hours, the solution is allowed to cool and the precipitate is filtered off.

25.7 g (=97% of theory) of the compound described above are obtained.

Melting point: 228° C. (with decomposition).

Example 2

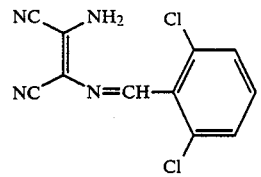

(Substance without information on a biological activity, known from J. Org. Chem. 39, No. 16,2344 (1974).

A mixture of 10.8 g of 2,3-diaminomaleic acid nitrile and 17.5 g of 2,6-dichlorobenzaldehyde is brought to the boiling point in 100 ml of acetonitrile. Thin layer chromatography indicates the end of the reaction after 4 hours. After cooling, 24.2 g (91% of theory) of the title compound are filtered off with suction. The substance (yellow-green needles) has a melting point of 191° C.

The following new compounds were obtained analogously to the abovementioned examples:

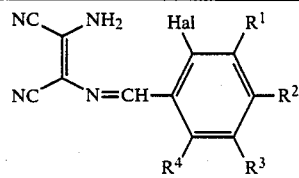

(I)

| Example No. | Hal | $R^1$ | $R^2$ | $R^3$ | $R^4$ | Melting point °C. or TR data |
|---|---|---|---|---|---|---|
| 3 | Cl | H | $CF_3$ | H | H | 189 |
| 4 | Cl | H | H | H | H | 190(Decomp.) |
| 5 | Cl | H | Cl | H | Cl | 234(Decomp.) |
| 6 | Cl | Cl | $CF_3$ | H | Cl | 198(Decomp.) |
| 7 | Cl | H | $COOCH_3$ | H | Cl | 179 |
| 8 | Cl | $CF_3$ | Cl | H | H | 113 |
| 9 | Br | H | Br | H | Br | 304 |
| 10 | Cl | H | Br | H | Cl | 3400/3300 ($NH_2$) |
| 11 | Cl | H | Cl | H | Br | 2280/2230 (CN) |
| 12 | Cl | H | $CF_3$ | H | Cl | 2300/2240 (CN) |
| 13 | Cl | H | $OCF_3$ | H | Cl | 3430/3310 ($NH_2$) |
| 14 | Cl | H | $OCCl_3$ | H | Cl | 3420/3300 ($NH_2$) |
| 15 | Cl | H | $OCF_3$ | H | H | 2250/2210 (CN) |
| 16 | Cl | H | $OCCl_3$ | H | H | 1605 (C=C) |
| 17 | Cl | H | $OCH_3$ | H | Cl | 3430/3300 ($NH_2$) |
| 18 | Cl | H | $OCH_3$ | H | H | 2240/2200 (CN) |
| 19 | Cl | H | $SCF_3$ | H | Cl | 2250/2210 (CN) |
| 20 | Cl | H | $SO_2CF_3$ | H | Cl | 1320 ($-SO_2-$) |
| 21 | Cl | H | $SCF_3$ | H | H | 3400/3300 ($NH_2$) |
| 22 | Cl | H | $SO_2CF_3$ | H | H | 1315 ($-SO_2-$) |
| 23 | Cl | H | H | H | $CH_3$ | 1370 ($CH_3$) |
| 24 | Cl | H | $CF_3$ | H | $CH_3$ | 1375 ($CH_3$) |
| 25 | Cl | H | $OCF_3$ | H | $CH_3$ | 1380 ($CH_3$) |
| 26 | Cl | H | $SO_2CF_3$ | H | $CH_3$ | 1375 ($CH_3$) |
| 27 | Cl | H | $SCF_3$ | H | $CH_3$ | 1375 ($CH_3$) |
| 28 | Cl | H | H | H | CN | 2210/2250/2200 (CN) |
| 29 | Cl | H | CN | H | Cl | 2200/2240/2250 (CN) |
| 30 | Cl | H | H | $NO_2$ | H | 266 |
| 31 | F | F | F | F | F | 198 |
| 32 | Cl | H | H | H | F | 184 |
| 33 | $CF_3$ | H | H | H | $CF_3$ | 190 |
| 34 | F | H | H | H | F | 217 |
| 35 | F | $CF_3$ | F | F | F | 152 |
| 36 | Cl | H | Cl | $OCF_3$ | Cl | 163 |

Example A

Tetranychus test (resistant)

Solvents: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Bean plants (Phaseolus vulgaris) which are heavily infested with the common spider mite or two-spotted spider mite (Tetranychus urticae) in all stages of development are treated by being dipped into the preparation of the active compound of the desired concentration.

After the specified period of time, the destruction in % is determined. 100% means that all the spider mites have been killed; 0% means that none of the spider mites have been killed.

In this test, for example, the following compounds from the preparation examples have an outstanding action against Tetranychus urticae (2)

TABLE
(mites which damage plants)
Tetranychus test

| Active compounds | Active compound concentration in % | Degree of destruction after 7 days in % |
|---|---|---|
| 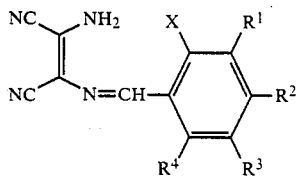 (2) | 0.1 | 98 |

It will be appreciated that the instant specification and claims set forth by way of illustration and not limitation, and that various modifications and changes may be made without departing from the spirit and scope of the present invention.

What is claimed is:

1. An azomethine of 2,3-diaminomaleic acid nitrile of the formula

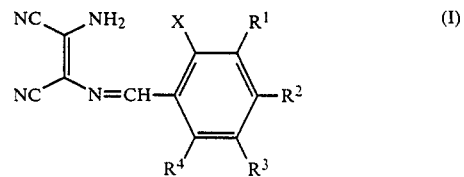

in which
X and $R^4$ each independently is fluorine, chlorine, bromine, iodine, $CF_3$ or CN, and
$R^1$ and $R^2$ and $R^3$ each independently is hydrogen, alkyl($C_1$-$C_4$), halogenoalkyl($C_1$-$C_4$), alkoxy($C_1$-$C_4$), halogenalkoxy($C_1$-$C_4$), halogen, CN, $NO_2$, dialkyl($C_1$-$C_4$)amino, alkoxy($C_1$-$C_4$)carbonyl, alkyl($C_1$-$C_4$)thio, alkyl($C_1$-$C_4$)thionyl, dihalogenoalkyl($C_1$-$C_4$) amino, alkyl($C_1$-$C_4$)sulphonyl, OH, SH or NH and at least one of $R^1$, $R^2$ and $R^3$ is haloalkoxy, alkoxycarbonyl, dihaloalkylamine or SH.

2. A compound according to claim 1, wherein at least three of $R^1$, $R^2$, $R^3$ and $R^4$ are not hydrogen.

3. A compound according to claim 1, wherein such compound is amino-2,4,6-trichloro-3-methoxy-toluylideneaminomaleic acid nitrile of the formula

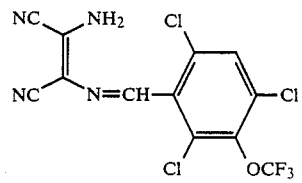

4. An acaricidal composition comprising an acaricidally effective amount of an azomethine of 2,3-diaminomaleic acid nitrile according to claim 1 and a diluent.

5. A method of combating acarids which comprises applying to such acarids or to an acarid habitat an acaricidally effective amount of an azomethine of 2,3-diaminomaleic acid nitrile of the formula $$\begin{array}{c}NC\diagdown\phantom{N}NH_2\phantom{=}X\phantom{==}R^1\\NC\diagup\phantom{N}N=CH-\phantom{=}R^2\\\phantom{========}R^4\phantom{=}R^3\end{array}\qquad(I)$$

in which
X and $R^4$ each independently is fluorine, chlorine, bromine, iodine, $CF_3$ or CN, and
$R^1$, $R^2$ and $R^3$ each independently is hydrogen, alkyl($C_1$-$C_4$), halogenoalkyl($C_1$-$C_4$), alkoxy($C_1$-$C_4$), halogenoalkoxy($C_1$-$C_4$), halogen, CN, $NO_2$, dialkyl($C_1$-$C_4$)amino, alkoxy($C_1$-$C_4$)carbonyl, alkyl($C_1$-$C_4$)thio, alkyl($C_1$-$C_4$)thionyl, dihalogenoalkyl($C_1$-$C_4$)amino, alkyl($C_1$-$C_4$)sulphonyl, OH, SH or $NH_2$.

6. The method according to claim 5, in which
X and $R^4$ each independently is fluorine, bromine, iodine or CF, and
two of $R^1$, $R^2$ and $R^3$ are hydrogen and the third is hydrogen, chlorine, bromine, iodine, cyano, nitro, methyl, ethyl, n- or i-propyl, n-, i-, s- or t-butyl, methoxy, ethoxy, methoxycarbonyl, ethoxycarbonyl, trifluoromethyl, trichloromethyl, pentafluoroethyl, trifluoroethyl, trifluoromethyl sulphone, trifluoromethoxy, trichloromethoxy, pentafluoroethoxy, dimethylamino, diethylamino, di-β-chloroethylamino or di-β-hydroxyethylamino.

7. The method according to claim 5, in which
X and $R^4$ each independently is chlorine or bromine, and
two of $R^1$, $R^2$ and $R^3$ are hydrogen and the third is chlorine, bromine, iodine, hydrogen, cyano, nitro, methyl, ethyl, n- or i-propyl, methoxy, ethoxy, methoxycarbonyl, ethoxycarbonyl, trifluoromethyl, trichloromethyl, dimethylamino, diethylamino or trifluoromethyl.

8. The method according to claim 5, in which
X and $R^4$ each independently is chlorine or bromine, and
two of $R^1$, $R^2$ and $R^3$ are hydrogen and the third is hydrogen, chlorine, bromine, methyl, cyano, trichloromethyl, trifluoromethyl, methoxy, trifluoromethoxy, trichloromethoxy or trifluoromethyl sulphone.

9. The method according to claim 5, in which

X is Cl,

R⁴ is chlorine or bromine, and two of R¹, R² and R³ are hydrogen and the third is hydrogen, chlorine, methyl, trichloromethyl, trifluoromethyl, methoxy, trichloromethoxy or trifluoromethoxy.

10. The method according to claim 5, wherein such compound is amino-2,6-dichlorotoluylideneaminomaleic acid nitrile of the formula

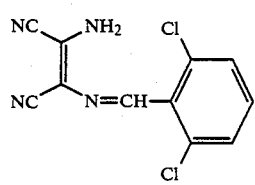

11. The method according to claim 5, wherein such compound is amino-2,4,6-trichlorotoluylideneaminomaleic acid nitrile of the formula

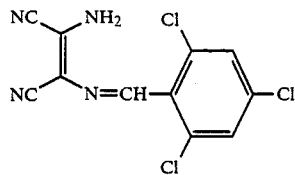

12. The method according to claim 5, wherein such compound is amino-2,4,6-trichloro-3-methoxytoluylideneaminomaleic acid nitrile of the formula

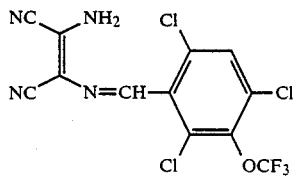

* * * * *